United States Patent
Verhoef

(10) Patent No.: US 8,000,799 B2
(45) Date of Patent: Aug. 16, 2011

(54) IN-HOME REMOTE MONITOR WITH SMART REPEATER, MEMORY AND EMERGENCY EVENT MANAGEMENT

(75) Inventor: William D. Verhoef, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/907,101

(22) Filed: Oct. 19, 2010

(65) Prior Publication Data
US 2011/0037614 A1 Feb. 17, 2011

Related U.S. Application Data

(62) Division of application No. 10/957,463, filed on Oct. 1, 2004, now Pat. No. 7,840,275.

(51) Int. Cl.
*A61N 1/08* (2006.01)
(52) U.S. Cl. .................................................. 607/60
(58) Field of Classification Search .............. 607/30–32, 607/59–60
See application file for complete search history.

(56) References Cited

U.S. PATENT DOCUMENTS

| | | | |
|---|---|---|---|
| 5,682,379 A | 10/1997 | Mahany et al. | |
| 5,890,055 A | 3/1999 | Chu et al. | |
| 5,944,659 A | 8/1999 | Flach et al. | |
| 6,497,655 B1 | 12/2002 | Linberg et al. | |
| 6,577,901 B2 | 6/2003 | Thompson | |
| 6,741,856 B2 | 5/2004 | McKenna et al. | |
| 6,773,344 B1 | 8/2004 | Gabai et al. | |
| 6,985,771 B2 | 1/2006 | Fischell et al. | |
| 7,024,249 B2* | 4/2006 | Weisner et al. | 607/60 |
| 7,060,031 B2 | 6/2006 | Webb et al. | |
| 7,065,409 B2 | 6/2006 | Mazar | |
| 7,200,134 B2 | 4/2007 | Proctor, Jr. et al. | |
| 7,230,935 B2 | 6/2007 | Proctor, Jr. et al. | |
| 7,263,335 B2 | 8/2007 | Leabman | |
| 2001/0031997 A1 | 10/2001 | Lee | |
| 2001/0049544 A1 | 12/2001 | Lee | |
| 2002/0045804 A1 | 4/2002 | Christopherson et al. | |
| 2003/0220673 A1 | 11/2003 | Snell | |
| 2004/0122487 A1* | 6/2004 | Hatlestad et al. | 607/60 |
| 2004/0152953 A1 | 8/2004 | Goedeke | |
| 2005/0256963 A1 | 11/2005 | Proctor, Jr. et al. | |
| 2008/0140160 A1 | 6/2008 | Goetz et al. | |

* cited by examiner

*Primary Examiner* — Scott Getzow
*Assistant Examiner* — Amanda Patton

(57) ABSTRACT

A remote patient monitoring system is provided including an implantable medical device (IMD) capable of collecting and storing medical data and multiple, networked external monitoring devices adapted for wireless communication with the IMD. The networked monitoring devices may be configured such that one device is the master and remaining devices are repeater units wherein the master monitoring device coordinates communication between the networked devices and the IMD based on maximizing the received transmission signal strength between the IMD and the monitoring device network. The system may further include a data communications network coupled to at least one of the multiple external monitoring devices to allow data to be transferred to a database or other communication medium. Likewise, data may be received by the monitoring device network from a database or other communication medium to be transferred to the IMD.

7 Claims, 4 Drawing Sheets

IN-HOME REMOTE MONITOR WITH SMART REPEATER, MEMORY AND EMERGENCY EVENT MANAGEMENT

This application is a divisional of U.S. patent application Ser. No. 10/957,463, filed Oct. 1, 2004, now U.S. Pat. No. 7,840,275, the disclosure of which is incorporated by reference in its entirety herein.

FIELD OF THE INVENTION

The present invention relates generally to a remote patient monitoring system and more particularly to a remote patient monitoring system including a network of multiple external monitors capable of bidirectional communication with a medical device and an associated method for coordinating the communication between the external monitor network and the medical device.

BACKGROUND OF THE INVENTION

One goal of a technology-based health care system that fully integrates the technical and social aspects of patient care and therapy is to connect the client with care providers irrespective of separation distance or location of the participants. While clinicians will continue to treat patients in accordance with accepted medical practice, developments in communications technology are making it ever more possible to provide medical services in a time- and place-independent manner.

Past methods of clinical services are generally limited to in-hospital operations. For example, if a physician needs to review the performance parameters of an implantable device in a patient, the patient normally has to go to the clinic. Further, if the medical conditions of a patient with an implantable device warrant continuous monitoring or adjustment of the device, the patient would have to stay in a hospital indefinitely. Such a continued treatment plan poses both economic and social problems. Under the exemplary scenario, as the segment of the population with implanted medical devices increases many more hospitals/clinics and service personnel will be needed to provide in-hospital service for the patients, thus escalating the cost of healthcare. Additionally the patients will be unduly restricted and inconvenienced by the need to either stay in the hospital or make very frequent visits to a clinic.

Yet another condition of the past practice requires that a patient visit a clinical center for occasional retrieval of data from the implanted device to assess the operations of the device and gather patient history for both clinical and research purposes. Such data is acquired by having the patient in a hospital/clinic to download the stored data from the implantable medical device. Depending on the frequency of data collection, this procedure may pose difficulty and inconvenience for patients who live in rural areas or have limited mobility. Similarly, in the event a need arises to upgrade the software of an implantable medical device, the patient will be required to come into the clinic or hospital to have the upgrade installed.

A number of proposals have been made to enable remote programming and monitoring of an IMD from a centralized patient management center. Such systems generally rely on an in-home remote monitor having bidirectional communication with the implanted device for retrieving data from the IMD. The in-home remote monitor (IRM) is coupled to a data communication network to enable transfer of retrieved data to a centralized database or medical support network. Depending on the communication schemes used, patient intervention may be required to accomplish a data transfer between the IMD and the IRM and/or between the IRM and the centralized patient management system.

With the use of long-range telemetry systems, patient intervention may not be required to initiate retrieval of data from the IMD although transmission from the IMD to the IRM may only be accomplished when the patient is within the communication range of the IRM. Thus a patient is required to remain compliant and cooperative in performing remote monitoring or programming sessions using an IRM, which can pose inconvenience and burden to the patient. Furthermore, if a patient is incapacitated due to a clinical event, the patient may be unable to initiate a remote monitoring session. A patient having a serious or life-threatening clinical event at home may be unable to contact help or send an IMD data transmission. There remains a need, therefore, for seamless and passive data transfer from a remote IMD to a centralized patient management system.

BRIEF SUMMARY OF THE INVENTION

The present invention provides a remote patient monitoring system including a network of multiple IRMs having coordinated communication with a medical device and with each other. The medical device, which may be an implantable medical device (IMD), is capable of acquiring and storing medical data and/or transferring real-time medical data. Each of the networked IRMs is capable of bi-directional, wireless communication with the IMD to enable data transmission between the IRM and IMD. Each of the networked IRMs are further capable of wireless communication with at least one other of the multiple IRMs using a transmission signal frequency that is different than the IMD-to-IRM transmission signal frequency.

In one embodiment, the IRM network includes one IRM configured as a master IRM in addition to one or more IRMs configured as repeater IRM units. The master IRM coordinates communication functions between the repeater units and the IMD. The master IRM monitors the transmission signal strength detected between each of the repeater IRM units and the IMD and selects the repeater IRM unit having the greatest signal strength for retrieving data from the IMD. The transmission signal strength between IRMs and the IMD is monitored, either continuously or during a data retrieval transmission. If the transmission signal strength between an IRM that is selected for data transmission weakens, a new IRM associated with the greatest signal strength is selected and data transfer is handed-off between IRM units.

At least one IRM included in the IRM network, typically the master IRM, is coupled to a data communication network for transferring data to a centralized patient management system and for transferring alert messages to the patient, a clinic, clinician, or other third party. The master IRM collects data retrieved from all repeater IRM units, performs any data conversion required for compatibility with the associated data communication network, and transfers all data to the centralized patient management system.

Each IRM includes telemetry circuitry for communicating with the associated medical device, telemetry circuitry for communicating with the IRM network and control circuitry such as a microprocessor and associated memory for controlling IRM functions. A networked IRM may include a display for displaying information relating to communication functions. IRM units may additionally be provided with long-term memory to allow data to be stored until adequate communication links are available for data transfer. At least one IRM in the IRM network is enabled to transfer data to a central database and may additionally be coupled to a communication network for sending alert notifications to the patient, medical personnel, emergency responders, or other third parties.

DETAILED DESCRIPTION OF THE PREFERRED EMBODIMENTS

Figure 1:
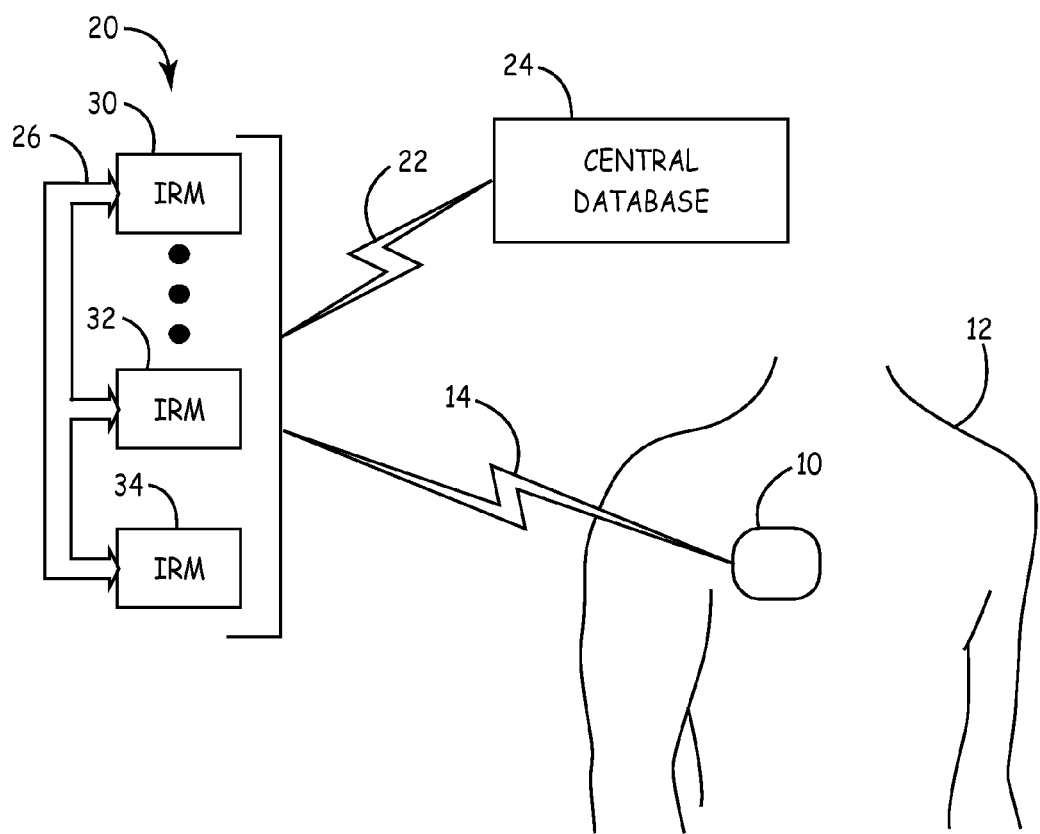
FIG. 1 is a diagram of a remote patient monitoring system including an IRM network.

FIG. 1 is a diagram of a remote patient monitoring system. An IRM network 20 as provided by the present invention may be used in conjunction with any medical device used for monitoring physiological conditions or treating a medical condition. The medical device may be an internal or an external medical device. An external medical device may be wearable by the patient and may be, for example, an ECG monitor, blood pressure monitor, respiration monitor or other external device. In the exemplary embodiments described herein, an IRM network 20 is described in conjunction with an implantable medical device 10.

IMD 10 is shown implanted in a patient 12. The simplified illustration of IMD 10 may represent a variety of IMDs such as cardiac pacemakers, implantable cardioverter defibrillators, hemodynamic monitors, ECG recorders, drug delivery devices, or neuromuscular stimulators. IMD 10 may be coupled to one or more leads and/or fluid delivery catheters which may be used for delivering a therapy such as an electrical stimulation therapy or drug therapy. Leads and/or catheters can carry electrodes or other physiological sensors used for monitoring one or more physiological signals for patient monitoring and for determining when therapy delivery is required. IMD 10 may alternatively be embodied as a leadless device wherein sensors or electrodes are incorporated in or on the housing of IMD 10. Examples of leadless monitoring devices are generally disclosed in U.S. Pat. No. 5,404,877 issued to Nolan et al., and U.S. Pat. No. 5,987,352 issued to Klein et al, both of which patents are incorporated herein by reference in their entirety. IMD 10 is provided with an antenna and associated circuitry, as will be described below, for establishing a communication link 14 with any of the multiple external, IRMs 30, 32, 34 included in IRM network 20.

An IRM network may be implemented in a patient's home making continuous remote patient monitoring possible while the patient is at home. Monitors 30, 32, and 34 are referred to herein as "in-home" remote monitors, however, the implementation of a network of monitoring units as described herein is not limited to practice within a patient's home. A patient monitoring system including a network of monitoring units may be installed in a clinic, hospital, or other public or private, indoor or outdoor, space.

As will be described in greater detail herein, data acquired by IMD 10 can be transferred from IMD 10 to any of IRMs 30, 32, and 34 through communication link 14. IRMs 30, 32, and 34 are enabled to communicate with each other via communication link 26. Communication link 26 is established using a different transmission signal frequency than the IMD-to-IRM communication link 14 such that communication between IRMs 30, 32 and 34 included in IRM network 20 does not interfere with communication between IMD 10 and any of IRMs 30, 32 and 34. Communication link 26 within IRM network 20 allows the individual IRMS, 30, 32 and 34, to communicate with each other for relaying data between IRMs 30, 32 and 34 as necessary during communication operations and for determining which IRM 30, 32 or 34 is receiving the strongest transmission signal from IMD 10.

In an exemplary embodiment, each IRM 30, 32, and 34 is configured to function as a master IRM or as a repeater or "slave" IRM. The master or repeater function may be selected by a user using a switch. The master IRM polls the repeater IRMs for a received signal strength indicator (RSSI), which indicates the strength of the transmission signal received from the IMD by any given IRM. The individual IRM having the strongest RSSI is enabled by a signal from the master IRM for transferring data to or from IMD 10. If the signal strength weakens during a data transmission, for example due to movement of the patient away from the active IRM, the master IRM re-evaluates the RSSI from all repeater IRMs. The IRM associated with the strongest transmission signal strength then becomes the active IRM for communication with IMD 10. Hence, IMD 10 is communicating with only one IRM at any one time, but the individual IRMs 30, 32 and 34 may be communicating with each other continuously at a different transmission frequency to maintain seamless data transmission between IMD 10 and the IRM network 20. As the received signal strength varies, communication with IMD 10 is "handed off" between IRMs to maintain the highest transmission signal strength throughout a data transfer.

At least the master IRM is additionally adapted to communicate with a centralized patient management system or database 24 to allow data received from IMD 10 to be transferred to the central database 24. A central database may be an Internet-based or other networked database used for remote patient monitoring. One of IRMs 30, 32, or 34 may transfer data via a communication link 22, which may be established via the Internet, a local area network, a wide area network, a telecommunications network or other appropriate communications network, which may be a wireless communication link. Examples of communication schemes for use in remote monitoring systems are generally disclosed in U.S. Pat. No. 6,599,250 issued to Webb et al., U.S. Pat. No. 6,442,433 issued to Linberg, and U.S. Pat. No. 6,574,511 issued to Lee, U.S. Pat. No. 6,480,745 issued to Nelson et al., U.S. Pat. No. 6,418,346 issued to Nelson et al., and U.S. Pat. No. 6,250,309 issued to Krichen et al., all of which patents are incorporated herein by reference in their entirety.

Figure 2:
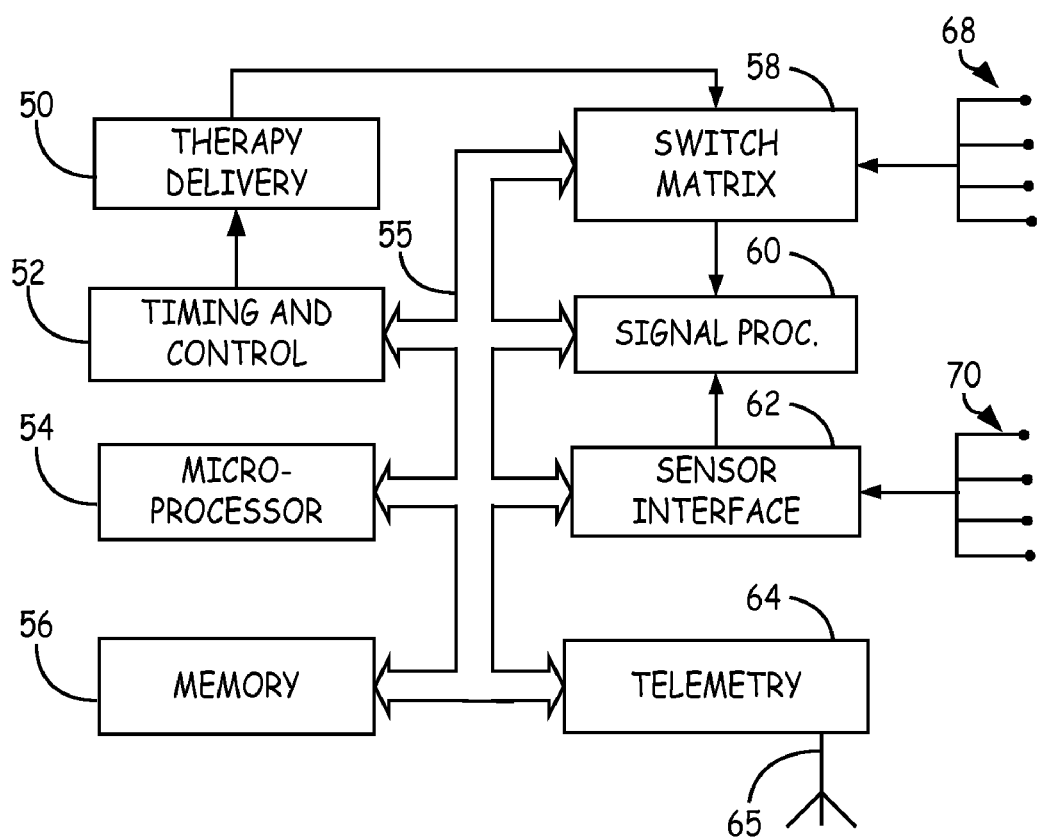
FIG. 2 is a block diagram of typical functional components of an IMD, such as the IMD shown in FIG. 1.

FIG. 2 is a block diagram of typical functional components of an IMD, such as IMD 10 shown in FIG. 1. IMD 10 generally includes timing and control circuitry 52 and an operating system that may employ microprocessor 54 or a digital state machine for timing and controlling sensing and therapy delivery functions in accordance with a programmed operating mode. Microprocessor 54 and associated memory 56 are coupled to the various components of IMD 10 via a data/address bus 55. IMD 10 may include therapy delivery unit 50 for delivering a therapy, such as an electrical stimulation or drug therapy, under the control of timing and control unit 52. In the case of electrical stimulation therapies, such as cardiac stimulation therapies, therapy delivery unit 50 is typically coupled to two or more electrodes 68 via a switch matrix 58. Switch matrix 58 is used for selecting which electrodes and corresponding polarities are used for delivering electrical stimulation pulses.

Electrodes 68 may also be used for sensing electrical signals within the body, such as cardiac signals, or for measuring impedance. In the case of cardiac stimulation devices, cardiac electrical signals are sensed for determining when an electrical stimulation therapy is needed and in controlling the timing of stimulation pulses.

Electrodes used for sensing and electrodes used for stimulation may be selected via switch matrix 58. When used for sensing, electrodes 68 are coupled to signal processing circuitry 60 via switch matrix 58. Signal processor 60 includes sense amplifiers and may include other signal conditioning circuitry and an analog-to-digital converter. Electrical signals may then be used by microprocessor 54 for detecting physiological events, such as detecting and discriminating cardiac arrhythmias. In some embodiments, cardiac arrhythmia detection, or detection of another serious or life-threatening event, may cause IMD 10 initiate a data transfer to an IRM.

In other embodiments, electrodes 68 may be used for measuring impedance signals for monitoring, for example, edema, respiration or heart chamber volume. Any of these signals may be used to detect a change indicating a worsening pathologic condition, which may trigger a transmission from IMD 10 to an IRM.

IMD 10 may additionally or alternatively be coupled to one or more physiological sensors 70. Such sensors may include pressure sensors, accelerometers, flow sensors, blood chemistry sensors, activity sensors or other physiological sensors known for use with IMDs. Sensors 70 are coupled to IMD 10 via a sensor interface 62 which provides sensor signals to signal processing circuitry 60. Sensor signals are used by microprocessor 54 for detecting physiological events or conditions. For example, IMD 10 may monitor heart wall motion, blood pressure, blood chemistry, respiration, or patient activity. Monitored signals may be used for sensing the need for delivering a therapy under control of the operating system. Physiological data may be recorded continuously by IMD 10 or upon a detected triggering event or change in a monitored physiological condition. Acquired physiological data may be stored for later transfer to an IRM or transferred in real-time. Any physiological signal may also be used to trigger a data transfer from IMD 10 to an IRM.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out on receipt of a retrieval or interrogation instruction. All of these functions and operations are known in the art, and many are generally employed to store operating commands and data for controlling device operation and for later retrieval to diagnose device function or patient condition. Microprocessor 54 controls device diagnostic functions, such as lead impedance monitoring, stimulation threshold testing, and device longevity estimation. Microprocessor 54 may also manage the storage of device performance parameters such as pacing capture success rate, frequency of delivered therapies, and response to delivered therapies. Device-related parameters acquired by IMD 10 may be transferred to an IRM and may be the basis for triggering a data transfer.

Microprocessor 54 may be programmed to generate an alert or alarm notifications in response to detecting predetermined physiological or device-related conditions or events. Such conditions or events may be set as triggering events for initiating an IMD-to-IRM data transfer. Data associated with the alert, as well other stored or real-time data, may be transferred to an IRM network.

In addition to facilitating the seamless retrieval of data from IMD 10 over a networked area, an IRM network may be used in remote programming operations. Operating parameters or programs stored in memory 56 and used by microprocessor 54 for controlling IMD functions may be programmed or updated remotely via the IRM network. Examples of remote programming methods which may utilize an IRM network for transferring data to an IMD are generally disclosed in U.S. Pat. No. 6,363,282 issued to Nichols et al., U.S. Pat. No. 6,497,655 issued to Linberg et al., all of which are incorporated herein by reference in their entirety, and previously incorporated U.S. Pat. No. 6,442,433 issued to Linberg et al. Thus, operating methods and parameters controlling IMD 10 functions may be updated in a timely manner in response to changes in disease state or currently available IMD programs.

IMD 10 is equipped with telemetry circuitry 64 and antenna 65 for bidirectional communication with the IRM network. Programming data and monitoring data are transmitted during downlink or uplink telemetry between IMD telemetry circuitry and external telemetry circuitry included in an IRM. As will be described in greater detail below, a networked IRM corresponding to the greatest transmission signal strength is selected from a number of networked IRMs for communicating with IMD 10. Communication with IMD 10 may be "handed-off" between networked IRMs as transmission signal strength changes. In an exemplary embodiment, telemetry circuitry 64 and antenna 65 are implemented as a long range telemetry system which allows IMD-to-IRM communication to occur without patient intervention, e.g. without the use of a programming head. Thus seamless communication between IMD 10 and networked IRMs may occur while the patient moves freely about the IRM networked area. Long-range telemetry systems are generally disclosed in U.S. Pat. No. 6,482,154 issued to Haubrich et al., U.S. Pat. No. 6,240,317 issued to Villaseca et al., and U.S. Pat. No. 6,169,925 issued to Villaseca et al., all of which patents are incorporated herein by reference in their entirety.

Figure 3A:
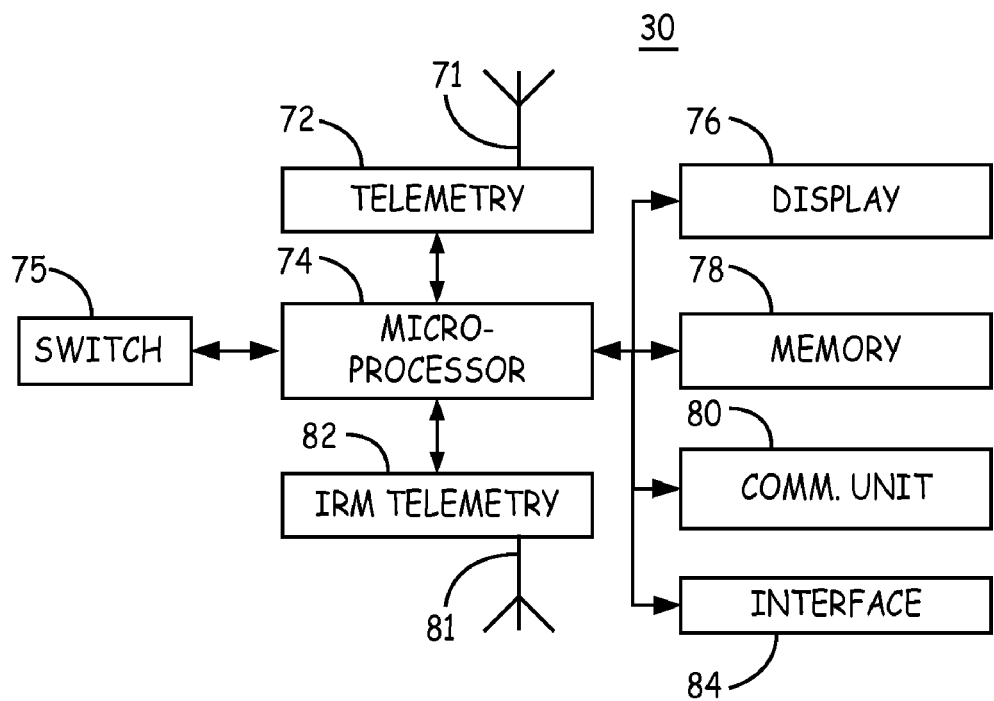
FIG. 3 is a simplified diagram of major functional blocks of an IRM for use in an IRM network.
Figure 3B:
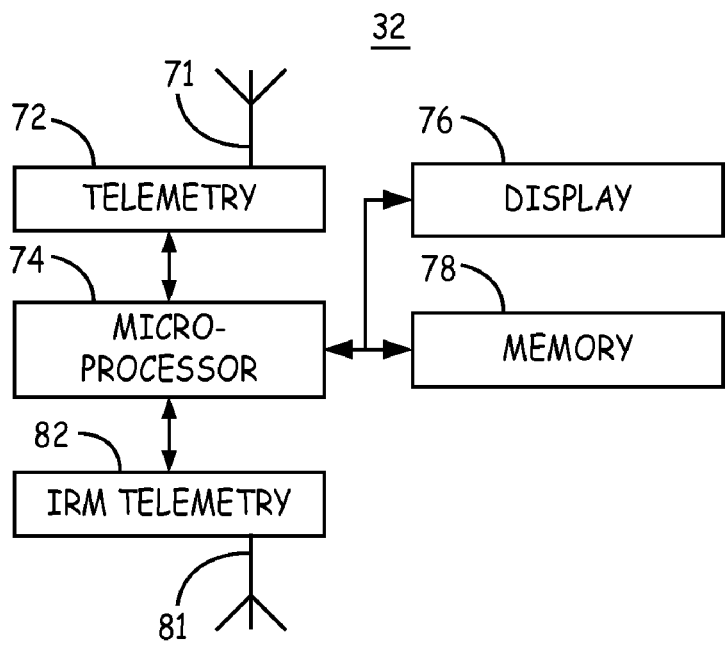

FIG. 3 is a simplified diagram of major functional blocks of an IRM 30 shown in FIG. 1. IRM 30 includes an RF telemetry antenna 71 coupled to a telemetry transceiver and antenna driver circuit board 72 including a telemetry transmitter and telemetry receiver. The telemetry circuitry 72 is coupled to and operated under the control of central processing circuitry, shown as a microprocessor 74 with associated memory 78. Telemetry circuitry 72 in conjunction with antenna 71 are used for bidirectional communication with an associated IMD or other medical device.

IRM 30 is provided with a second telemetry unit, including IRM telemetry circuitry 82 and antenna 81, used for IRM network communication. IRM telemetry circuitry 82 and antenna 81 may be designed and tuned for RF communication at a different frequency than the frequency used by the first telemetry circuitry 72 for communicating with an IMD. IRM network communication is not limited to RF telemetry schemes. In alternative embodiments, other modes of wireless communication may be implemented for creating a communication network between multiple IRMs. Single- or multi-channel schemes using any available communication protocol or modulation scheme that does not create interference with the telemetry transmission signal between the associated medical device and IRM 30 may be used.

IRM 30 is shown to include a display 76 which may be an audio or visual display. A visual display may be provided, for example, as a graphics display screen or LEDs. Display 76 can be used to indicate to a patient information relating to the communication functions of IRM 30 and the overall IRM network. For example, an LED or graphic display may be used to indicate when data transmission is occurring or has been completed between an associated IMD and IRM 30 or between IRM 30 and another networked IRM. The display may be configured to indicate which device is sending and which device is receiving during a data transmission. Display 76 may also be used to generally indicate the transmission signal strength. A display may indicate when a patient is within telemetry range of IRM 30 and when he/she is moving out of the telemetry range of IRM 30 or the signal is weakening. In this way, a patient may control his/her movements within the IRM networked area during data transmission. By displaying a received signal strength indicator, a patient may be cognizant of the effects of his/her movements through the IRM networked area. Such awareness will facilitate the placement of the master and repeater IRMs to fully cover a desired area or home and optimize communication between the IRM network and associated IMD. Display 76 may additionally be used to indicate which IRM within an IRM network is designated as the master IRM and/or which IRMs are repeater IRMs.

IRM 30 may additionally be provided with a communication unit 80 which may be in the form of a hard-wired or wireless modem. Monitoring data received by IRM 30 from an associated IMD can be transferred to a networked local or central database via communication unit 80. In response to receiving alert data from an IMD, the IRM network may send an alert notification and any pertinent data or patient information to the centralized database to notify medical personnel. The IRM network may additionally or alternatively send an alert notification to a patient, medical personnel or other caregiver via a phone call, electronic mail, fax, page or other communication medium via communication unit 80.

It is not necessary for all IRMs within an IRM network to be equipped with communication unit 80 for transferring data to a central database or for sending notifications via an appropriate communication network. In some embodiments, the designated master IRM is provided with communication unit 80. Data received by any of the repeater IRMs may be transferred to the master IRM via IRM telemetry circuitry 82 and subsequently transferred to a central database by the master IRM using communication unit 80. Likewise, remote programming data may be received by IRM 30 from a central patient management system via communication unit 80. Such data may then be relayed within the IRM network using IRM telemetry circuitry 82 to the IRM having the greatest RSSI with the IMD. The remote programming data is then transmitted by the IRM to the IMD via telemetry circuitry 72.

In other embodiments, IRM 30 may utilize the IRM telemetry circuitry 82 in place of a separate communication unit 80 for communications with electronics or networks outside of the IRM network. In addition to communicating with a central patient management database, IRM 30 may communicate with home electronic audiovisual or communication appliances, such as a handheld computing device, a personal or laptop computer, cellular phone, fax machine, DVD recorder, etc. Such communication allows transmission of alert notifications, viewing of monitoring data, or recording monitoring data. Communication between a monitoring or programming device and personal audiovisual or communication appliances is generally disclosed in U.S. patent application Ser. No. 09/745,112 to Ferek-Petric, incorporated herein by reference in its entirety. IRM telemetry circuitry 82 may be implemented using standardized wireless communication technology, such as Wi-Fi or Bluetooth, allowing IRM network communications with other electronics to be performed without additional linking hardware or requiring data conversion algorithms.

IRM 30 may optionally be provided with an interface 84 to enable connectivity with a personal computing device or other home or office appliance. IRM 30 may be directly coupled to a personal electronic device to allow transmission of data from IRM 30 to the electronic device. Such interfacing may simplify the transfer of data and enable easy viewing or storage of data locally. For example, IRM 30 may be interfaced with a personal computer to allow data received or stored by IRM 30 to be viewed locally off-line or in real time by the patient, a clinician, or other caregiver.

IRM 30 includes memory 78 for storing control programs and algorithms used in operating the communication functions of the IRM network. Memory 78 may further include data registers for storing monitoring data received from an associated IMD or remote programming data received from a central patient management system. Data storage capabilities allow received data to be stored until a communication link can be established for transferring data, either to the master IRM or to a central database or other data storage or recording unit. Stored data would not be lost in case of a power outage or other interruption or delay of IRM network communication. Display 76 may be used to indicate when pending data is stored in memory 78. Such pending data may include physiological event data, therapy delivery episodes, device diagnostic data, or alert notification.

Memory 78 may further be used for storing contact information for medical personnel, family members or other care providers. Contact information, such as IP addresses, may be used for transferring periodically acquired data for general monitoring purposes. In case an urgent medical or device-related event is detected by the IMD and such information is received by IRM 30, IRM 30 may place a phone call or send an electronic message via communication unit 80 to the appropriate contact. Memory 78 may be used to store voice recordings that may be played upon placing a phone call using communication unit 80. Voice recordings would provide relevant information such as patient name, location, type of emergency or medical event, and so on. In other embodiments, relevant information may be transferred electronically to an email address, website, fax machine, cellular text messaging number, or other communications device or destination. Such communication protocols for notifying the patient or a third party of pertinent medical information is performed under the control of microprocessor 74, typically by an IRM designated as the master IRM.

Each IRM included in an IRM network may be configured to operate as either the master IRM or a repeater IRM. Selection of master or repeater functions may be made using a switch 75 coupled to microprocessor 74 to enable functions performed by the master IRM such as coordinating communication of the networked IRMs, transferring data to a central database, or sending alert notifications. In other embodiments, repeater IRM units may be provided having limited functions in a smaller device. Such limited functionality includes at least communication with an associated medical device and communication with the IRM network.

IRMs included in the networked IRM system provided by the present invention may optionally include additional features available in commercially available programmer or in-home monitors. For example IRM 30 may be equipped with an interface module for coupling to other external monitoring or recording equipment. IRM 30 may be provided with a floppy disk drive, CD ROM drive or other electronic data storage medium. IRM 30 may further include a strip chart recorder or other data recording unit so that a record of received data can be generated. In order for a patient or other caregiver to communicate with IRM 30, a keyboard, pointing device, graphical user interface, or other user interface may be coupled to microprocessor 74. Through a user interface, commands for transmitting, storing, recording or displaying data may be entered.

Figure 4:
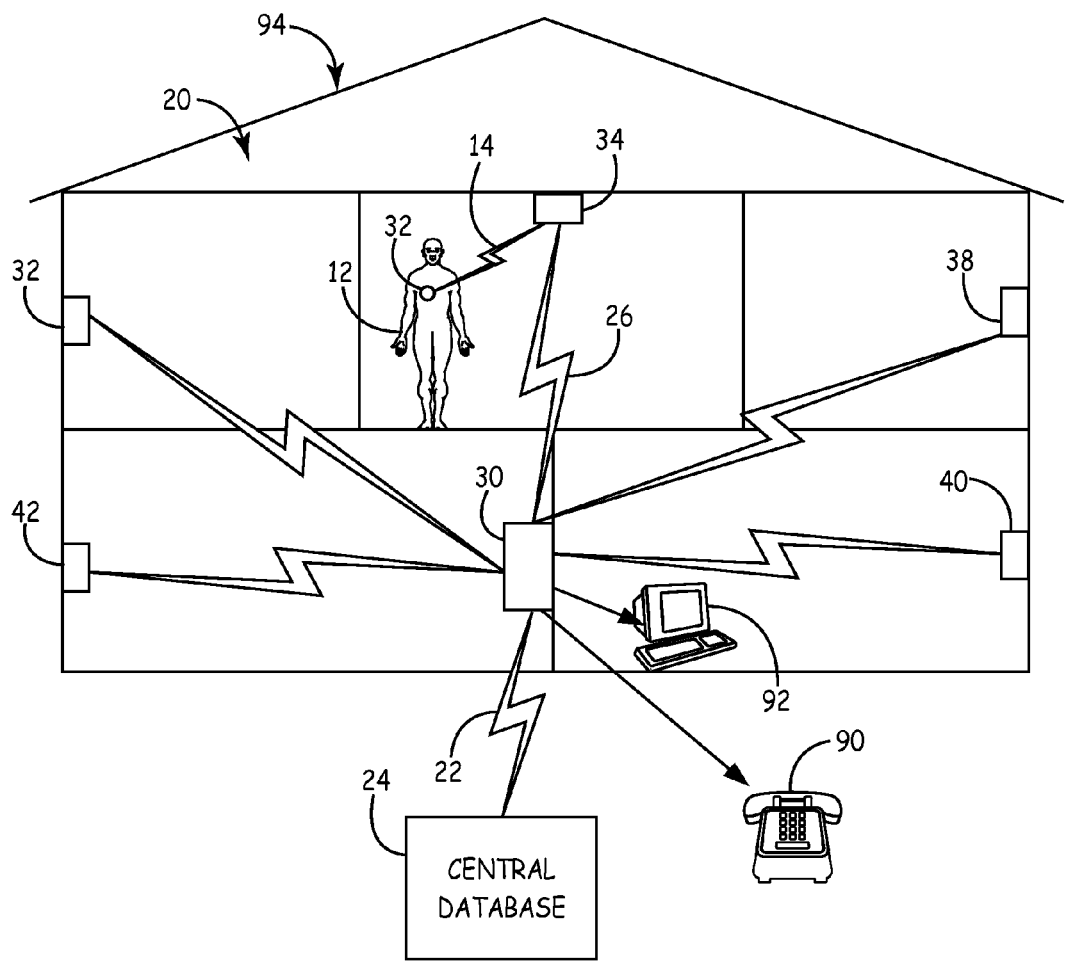
FIG. 4 is an illustration of one arrangement of an IRM network accordance with the present invention.

FIG. 4 is an illustration of one arrangement of an IRM network accordance with the present invention. An IRM network 20 may be installed in a home, hospital, clinic or any other public or private, indoor or outdoor space. In FIG. 4, an IRM network is shown installed in a patient's home to allow a patient 12 to move freely about the house 94 while continuously maintaining communicability between IMD 10 and the IRM network 20. The IRM network 20 includes an IRM 30 designated as the master IRM and multiple repeater IRMs 32, 34, 38, 40 and 42 positioned a distance from each other throughout the intended network space, house 94. The locations of master IRM 30 and repeater IRMs 32, 34, 38, 40 and 42 are sought to provide the best possible transmission signal strength between IMD 10 and the IRM network 20 as patient 10 goes about his/her daily activities. As noted previously, IRMs 30, 32, 34, 38, 40 and 42 may be equipped with a display for indicating to patient 10 the effect on signal strength as he/she moves about a room or the house. Such a display is useful in selecting locations for the IRMs 30, 32, 34, 38, 40 and 42. As shown in FIG. 4, IRM units may be configured to be wall- or ceiling mounted devices.

Each of IRMs 30, 32, 34, 38, 40 and 42 are capable of communicating with IMD 10 as previously described. Repeater IRMs 32, 34, 38, 40 and 42 are each able to communicate with master IRM 30. Repeater IRMs 32, 34, 38, 40 and 42 transmit a RSSI to master IRM 30. Master IRM 30 enables the IRM having the strongest RSSI as the active IRM for communicating with IMD 10. Master IRM 30 may continuously or periodically poll the active IRM to detect a weakening RSSI. Master IRM 30 would then poll the remaining IRMs to determine which IRM has the strongest RSSI and will re-assign the active IRM accordingly. Thus, IMD-to-IRM communication is seamless as patient 12 moves about house 94.

If monitoring data is received by a repeater IRM 32, 34, 38, 40 or 42, the repeater IRM establishes a communication link with the master IRM 30 to transfer the monitoring data. The data may be stored temporarily by an IRM until an IRM-to-IRM communication link is established. The repeater IRM transferring data may relay the data to the master IRM 30 via intervening repeater IRMs as necessary. If a data transmission was performed between IMD 10 and more than one IRM, due to changes in RSSI, each IRM transfers a packet of data to master IRM 30.

Once master IRM 30 has received a complete data transmission directly from IMD 10 and/or any of repeater IRMs 32, 34, 38, 40 and 42, master IRM 30 executes the appropriate communication functions. Depending on the data received, master IRM 30 may send data or information to central database 24 or a local database on a personal computer 92. Master IRM 30 may execute a telephone call, send an electronic message, or other communication to an appropriate list of contacts as described previously and may therefore be coupled to a telephone network 90 or other appropriate communication network.

Master IRM 30 may receive programming data from central database 24 for transfer to IMD 10. IRM 30 may transfer programming data directly to IMD 10 or poll repeater units 32, 34, 38, 40 and 42 to determine which IRM has the greatest RSSI. Master IRM 30 would then transfer programming data to the repeater unit having the strongest RSSI. The repeater IRM in turn would transmit data to the IMD 10.

Thus, a remote patient monitoring system has been described including a network of remote monitors for maintaining communicability with an associated medical device over a larger space than that covered by a single monitor. Such a system allows a patient to move freely about a home or other network-covered area while data transmissions occur between the medical device and IRM network without interruption. Continuous remote monitoring of a patient within a network-covered area can be realized without limiting the patient's movements or requiring the patient to wear an external monitoring device. Medical personnel or other caregivers can be notified promptly by the IRM network though selected communication mediums when serious or life-threatening events are detected by the IMD.

Various aspects of the present invention have been described herein according to detailed, illustrated embodiments. However it is recognized that numerous variations may be conceived for implementing a network of remote patient monitoring devices, wherein such devices may have varying degrees of complexity and features and may utilize any type of available communication and networking technologies. A remote patient monitoring network may be utilized with a variety of medical devices. The various embodiments described herein should therefore be considered exemplary, not limiting, with regard to the following claims.

What is claimed is:

1. A monitor for use in a remote patient monitoring system, comprising:
    a first telemetry unit for communicating with a medical device at a first transmission frequency, said first telemetry unit including a received signal strength indicator;
    a second telemetry unit for communicating with at least one other monitor at a second transmission frequency; and
    a signal strength monitor operable to monitor the signal strength indicator of the monitor and the signal strength indicator of the at least one other monitor, wherein the monitor is operable to select itself or the at least one other monitor to transfer data to or from the medical device.

2. The monitor of claim 1 further comprising a communication unit operable to be coupled to a communication network.

3. The monitor of claim 1 further comprising a memory operable to store data received from a medical device.

4. The monitor of claim 1 further comprising a display.

5. The monitor of claim 1 further comprising an interface operable to couple the monitor to an electronic appliance.

6. The monitor of claim 1 wherein the selected monitor having a stronger received signal strength indicator.

7. The monitor of claim 6 wherein a change of the selected monitor does not cause interruption of the communication with the medical device.

* * * * *